(12) United States Patent
Samuels et al.

(10) Patent No.: US 10,779,720 B2
(45) Date of Patent: Sep. 22, 2020

(54) DEVICE FOR NONINVASIVE DETERMINATION OF PATHOPHYSIOLOGICAL CONDITIONS

(71) Applicant: YuScan USA, LLC, Norcross, GA (US)

(72) Inventors: Mark A. Samuels, Johns Creek, GA (US); Nai-Teng Yu, Marietta, GA (US); Rick Fowler, Dacula, GA (US)

(73) Assignee: YUSCAN USA, LLC, Norcross, GA (US)

( * ) Notice: Subject to any disclaimer, the term of this patent is extended or adjusted under 35 U.S.C. 154(b) by 141 days.

(21) Appl. No.: 16/093,100

(22) PCT Filed: Mar. 24, 2017

(86) PCT No.: PCT/US2017/024133
§ 371 (c)(1),
(2) Date: Oct. 11, 2018

(87) PCT Pub. No.: WO2017/172534
PCT Pub. Date: Oct. 5, 2017

(65) Prior Publication Data
US 2019/0269314 A1    Sep. 5, 2019

Related U.S. Application Data

(60) Provisional application No. 62/390,323, filed on Mar. 26, 2016.

(51) Int. Cl.
*A61B 3/00* (2006.01)
*A61B 3/10* (2006.01)

(52) U.S. Cl.
CPC .............. *A61B 3/0008* (2013.01); *A61B 3/10* (2013.01); *A61B 3/0083* (2013.01)

(58) Field of Classification Search
CPC ....... A61B 3/0008; A61B 3/10; A61B 5/0071; A61B 5/0075; A61B 3/0083; A61B 5/14532
See application file for complete search history.

(56) References Cited

U.S. PATENT DOCUMENTS

2015/0335479 A1*  11/2015  Shibata .................. A61F 9/009
606/5

* cited by examiner

*Primary Examiner* — Wen Huang
(74) *Attorney, Agent, or Firm* — The Small Patent Law Group LLC; Josef L. Hoffmann (57) ABSTRACT

Implementations described herein include a device having a data collection system, an actuation assembly, and a visible target. The data collection system has an illuminator, a detector, and a beam splitter operably coupled to the detector. The actuation assembly is coupled to the illuminator via a holder and has a motor coupled to a linear actuator and a speed governor. The visible target facilitates alignment of the subject's eye with the data collection system. The illuminator illuminates the target tissue with interrogating radiation and the actuation assembly moves the illuminator from a first position to a second position to scan a focal point of the interrogating radiation through a predefined thickness of the target tissue. The detector detects the at least one value of the at least one characteristic of responding radiation received from or reflected from the target tissue and uses such information to determine the onset and duration of a pathological condition.

19 Claims, 5 Drawing Sheets

DEVICE FOR NONINVASIVE DETERMINATION OF PATHOPHYSIOLOGICAL CONDITIONS

RELATED APPLICATION

This application claims priority to U.S. Provisional Application No. 62/390,323 filed on Mar. 26, 2016, which is hereby incorporated by reference in its entirety.

FIELD

Implementations described herein include devices for noninvasive determination of the onset and duration of pathophysiological conditions and associated methods.

BACKGROUND

There are several blood based tests for determining whether a subject has diabetes, but there are no portable and simple to operate devices or methods that are specifically configured for use in resource-constrained settings to noninvasively detect early signs of diabetes.

SUMMARY

The present inventors have recognized, among other things, that a problem to be solved can include determining the presence of a pathophysiological condition via spectroscopic examination of the tissue of the eye in a subject and without the need for costly components, such as an eye tracker or scanning mechanism. The present subject matter can help provide a solution to this problem, such as by providing a device comprising a spectroscopic data collection system, an actuation assembly, a visible target. The data collection system can comprise an illuminator, a detector, and a beam splitter operably coupled to the detector. The actuation assembly can be coupled to the illuminator via a holder and can comprise a motor coupled to a linear actuator and a speed governor. The visible target can facilitate alignment of the subject's eye with the data collection system. The illuminator can illuminate the target tissue with interrogating radiation and the actuation assembly can move the illuminator from a first position to a second position to scan a focal point of the interrogating radiation through a predefined thickness of the target tissue. The detector can detect the at least one value of the at least one characteristic of responding radiation received from or reflected from the target tissue.

The present disclosure also provides for a method that can include the steps of: facilitating subject-self alignment of a target tissue relative to a device comprising: a data collection system comprising an illuminator, a detector and a beam splitter operably coupled to the detector; an actuation assembly coupled to the illuminator via a holder, the actuation assembly comprising a motor coupled to a linear actuator and a speed governor; and a visible target to facilitate alignment of the subject's eye with the data collection system; monitoring the target tissue to until the target tissue corresponds to a target position; illuminating the target tissue with the illuminator; moving the illuminator from a first position to a second position via the actuation assembly to scan a focal point of the interrogating light through a predefined thickness of the target tissue; detecting at least one characteristic of responding radiation received from or reflected from the target tissue; and correlating the at least one characteristic of responding radiation to determine specific diagnostic information comprising at least one of the presence, non-presence, onset, and duration of a pathological condition.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present subject matter can include devices configured for noninvasive determination of the presence, the onset, and the duration of pathophysiological conditions such as, but not limited to, diabetes, pre-diabetes, cataracts, and the like. The device can be portable. The present inventors have recognized, among other things, that a problem to be solved can include determining the presence, onset, and/or duration of a pathophysiological condition via an eye of a subject, and doing so without the need for costly components, such as an eye tracker or scanning mechanism. The present inventors appreciate that having devices that facilitate such determination and devices that are cost-effective and easy to use will enable diagnosis and treatment of a wide range of patients in a wide range of settings, greatly increasing the quality of life for many.

Figure 1A:
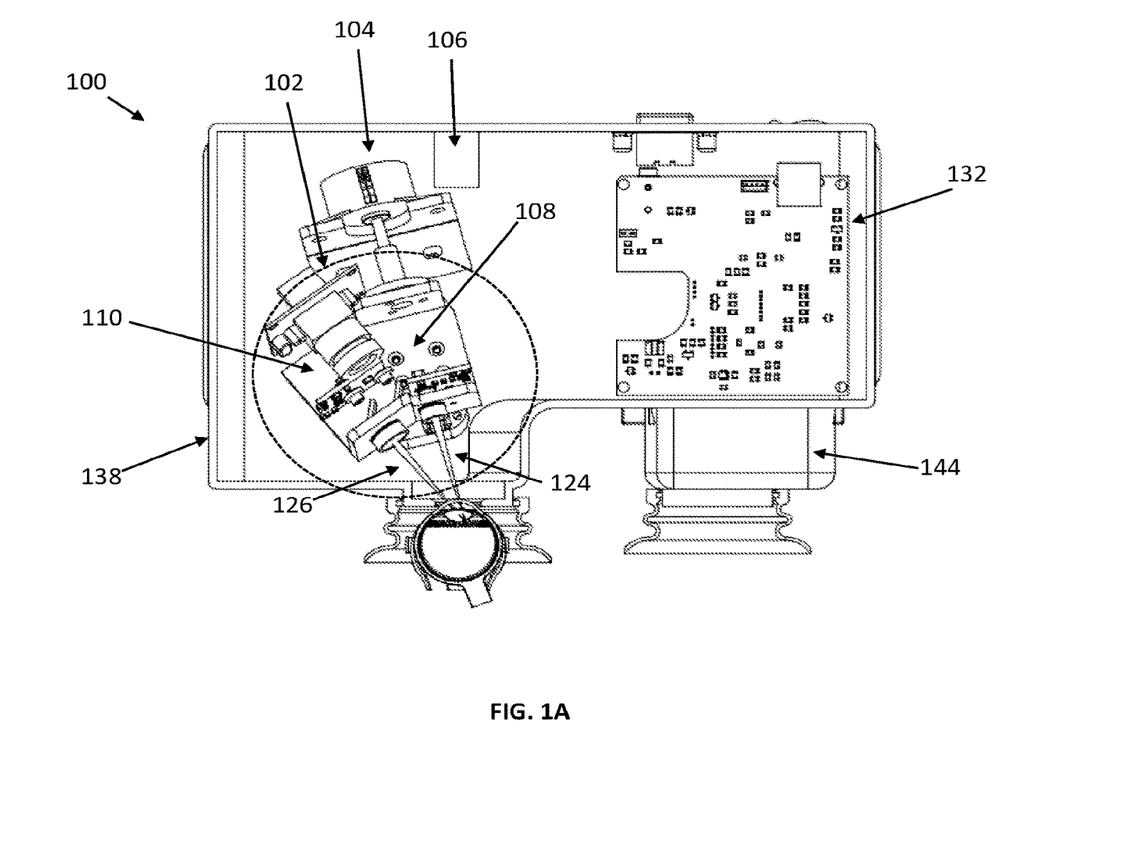
FIG. 1A illustrates one embodiment of a device for noninvasive determination of the onset and duration of pathophysiological conditions according to the present subject matter.
Figure 1B:
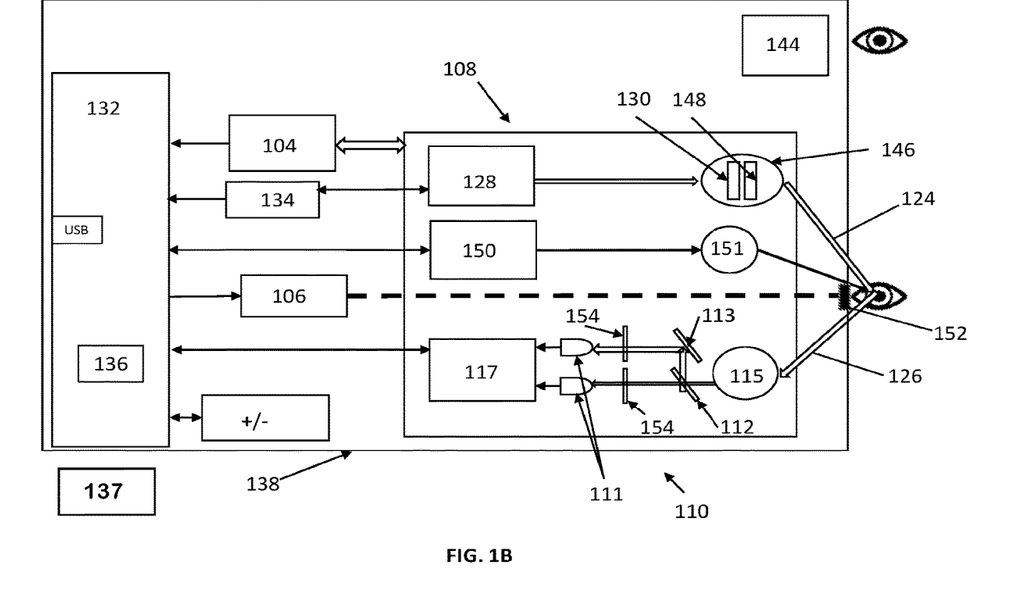
FIG. 1B illustrates the components of the embodiment illustrated in FIG. 1A.

As illustrated in FIG. 1, the present subject matter can provide a device 100 that can comprise a data collection system 102, an actuation assembly 104, and a visible target 106. The data collection system 102 can comprise an illuminator 108, a detector system 110, and a beam splitter 112 that can be operably coupled to the detector system 110. The detector system 110 can be a multipixel photon counter (MPPC) detector system and can comprise at least one detector 111 operably coupled to a beam splitter 112, a mirror 113, detector optics 115, and a detector receiver 117. Additionally or alternatively, the at least one detector 111 can comprise an avalanche photodiode. The detector 110 can also be operably coupled to at least one filter 154, such as, but not limited to, a Rayleigh filter or a fluorescence filter. The actuation assembly 104 can be coupled to the illuminator 108 via a holder 114 and can comprise a motor 116 coupled to a linear actuator 118. The visible target 106 can facilitate alignment of the target tissue, e.g., at least a portion of the subject's eye and, optionally, other turbid media such as the crystalline lens, with the data collection system 102 by providing a fixed spot or spots on which the subject can fix their gaze. The illuminator 108 can illuminate the target tissue with interrogating radiation 124 and the actuation assembly 104 can move the illuminator 108 from a first position to a second position to scan a focal point of the interrogating radiation 124 through a predefined thickness of the target tissue. The detector system 110 can detect at least one value of at least one characteristic of responding radiation 126 received from or reflected from the target tissue. The responding radiation 126 can comprise backscattered light, Rayleigh light, fluorescent light, or other light generated by the target tissue in response to illumination.

In operation, the illuminator 108 can provide for narrowband illumination of the target tissue and the at least one value of the at least one characteristic of responding radiation 126 can be compared to an expected value as described further below in order to determine the presence, the onset, and the duration of pathophysiological conditions such as, but not limited to, diabetes in the patient.

The at least one value of the at least one characteristic of the responding radiation 126 received from or reflected from the target tissue can comprise intensity or polarization anisotropy of the responding radiation 126 or temporal characteristics of the responding radiation 126. Temporal characteristics of the responding radiation 126 can comprise decay time of fluorescent emissions, phase shift characteristics, or the like. In one example, the at least one value of the at least one characteristic of the responding radiation 126 can include autoflourescence generated by the target tissue in response to the incident interrogating radiation 124. The intensity of the responding fluorescent light can be compared to an autoflourescence intensity expected for a specific control group of cohorts of a similar age, gender, or ethnicity that have not manifest the pathophysiological condition(s) of interest. An amount that the intensity of the responding autoflourescence deviates from an expected autoflourescence intensity for the control group can then be used to correlate, determine, or estimate the presence, the onset, and the duration of the pathophysiological condition(s) of interest. In another example, the at least one value of the at least one characteristic of the responding radiation 126 can include Rayleigh light backscattered from the target tissue and, optionally, autoflourescence of the target tissue generated by the target tissue in response to the incident interrogating radiation 124. Here, the intensity of the fluorescent component can be normalized to the intensity of the Rayleigh component by forming the ratio of the fluorescent intensity to the Rayleigh intensity. The relative amount of backscattered fluorescent and Rayleigh radiation can be a reliable indicator of the onset and progression of diseases such as diabetes, prediabetes, cataracts, and the like humans and animals.

The illuminator 108 can comprise light source 128 comprising a light-emitting diode or a laser diode. The illuminator 108 can further comprise a first lens 130 positioned with respect to the light source to produce interrogating radiation 124. The illuminator 108 can further comprise a lens system 146 comprising the first lens 130, at least one second lens 148, and an aperture 152 at the lens system focus that can have a diameter of at least about 15 micrometers.

Here, the first lens 130 or the lens system 146 can be optically responsive to the interrogating radiation 124. Additionally or alternatively, the illuminator 108 can include an operating wavelength of from about 400 to about 600 nm, and, more particularly, of from about 400 to about 460 nm. In one example, the illuminator 108 can include an operating wavelength of 434 nm and a tolerance of about 10 nm. In another example, the illuminator 108 can include an operating wavelength of 472 nm and a tolerance of about 10 nm.

The device 100 can optionally comprise a data processing system 132. The data processing system 132 can comprise a transmitter 134 that wirelessly and securely transmits the at least one characteristic of responding radiation to a remotely-located computational system 136. The data processing system 132 can further comprise a transmitter/receiver unit 136 for wirelessly transmitting receiving specific diagnostic information from a remotely-located computational system 137, such as a Bluetooth chip, or the like. It is further contemplated that the data collection system 102 or the data processing system 132 can receive and account for patient-specific inputs such as a patient's age, gender, ethnicity, physical characteristics, and the like to further account for in conjunction with the at least one value of the at least one characteristic of responding radiation 126. The data processing system 132 can also comprise a USB port or the like in order to communicate or transfer data with other computational systems or data input devices.

Figure 2:
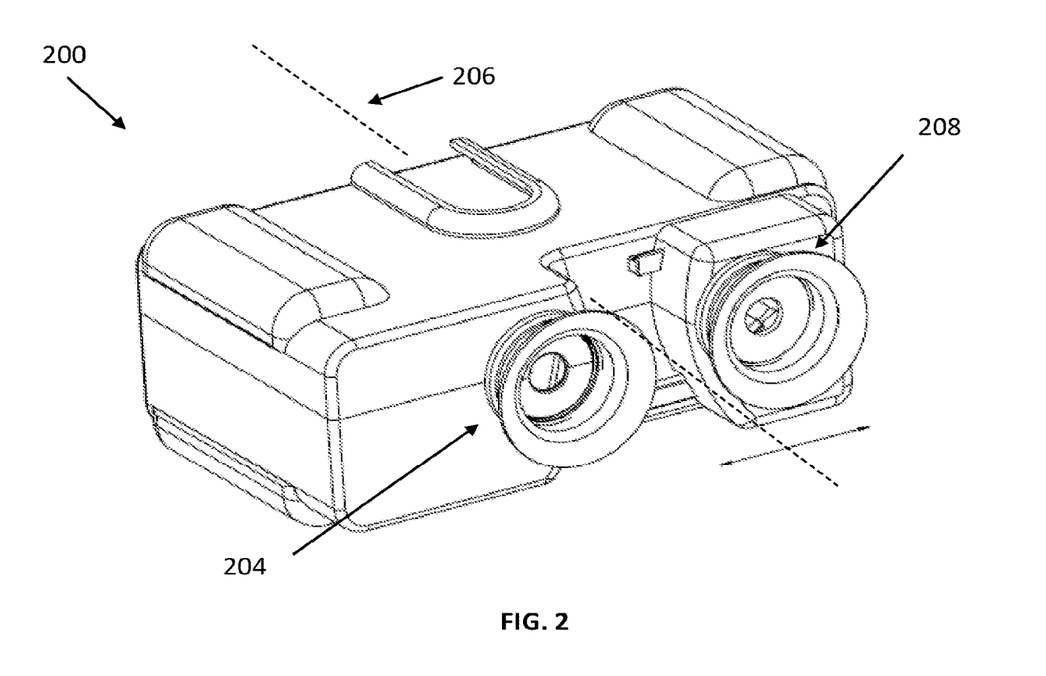
FIG. 2 illustrates another embodiment of a device for noninvasive determination of the onset and duration of pathophysiological conditions according to the present subject matter.

The device 100 can be monocular. In one embodiment, the device 100 can comprise a housing 138 comprising a sliding barrier 144. The housing 138 can selectively isolate and interrogate the left or the right eye of a subject for analysis. In another embodiment illustrated in FIG. 2, the device 200 can be substantially as described with regard to FIG. 1 but comprise a housing 202 that can have a barrier 204 to selectively isolate the left or the right eye of a subject for analysis. Here, the housing 202 can be rotated 180 degrees about an axis 206 extending from a distal end to a proximal end thereof in order to selectively isolate and interrogate the left or the right eye.

Referring back to FIG. 1, the device 100 can further comprise a channel 150 and associated channel optics 151 for collecting the image of a retina through the crystalline lens and processed this image to determine if the retina is normal and if cataracts are present. The data collection system 102 or the data processing system 132 can be further configured to evaluate the percentage of loss of light through the eye due to cataracts.

Figure 3:
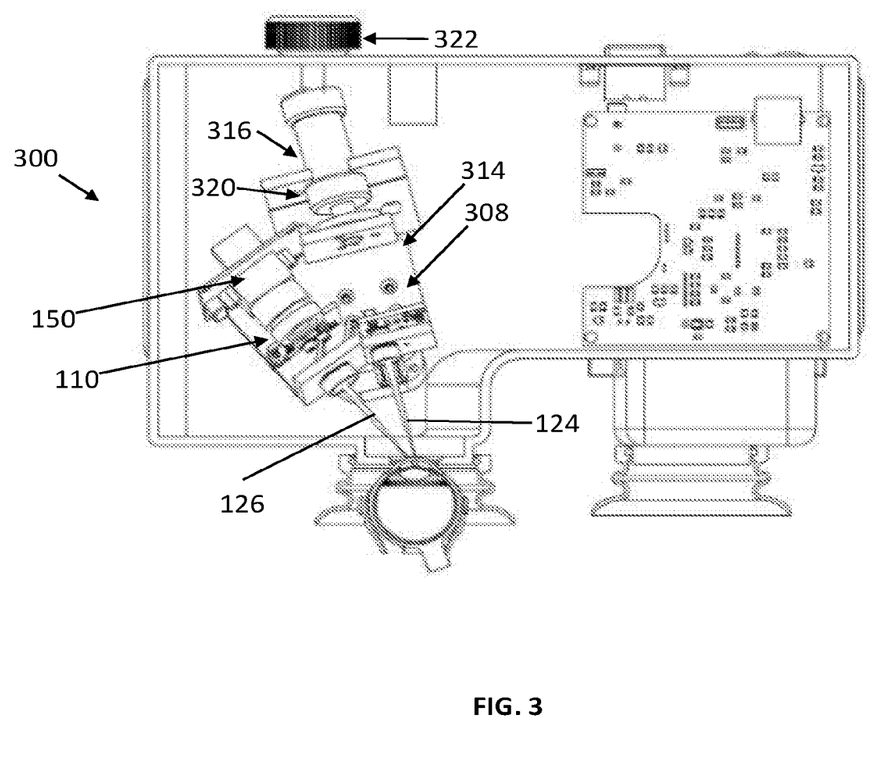
FIG. 3 illustrates another embodiment of a device for noninvasive determination of the onset and duration of pathophysiological conditions according to the present subject matter.

As illustrated in FIG. 3, the device 300 can be substantially as described above but can further comprise an actuation assembly 304 including a motor 316 comprising an electromechanically actuated motor or a spring wound motor. The motor 316 can optionally further comprise a manual tensioner 322 coupled to the motor that is adjustable by a user, such as, for example and without limitation, a spring tensioner and the like. Additionally or alternatively, the actuation assembly 304 can further comprise a speed governor 320 operably coupled to the linear actuator 318. In one example, the linear actuator 318 can be coupled to a wind-up spring motor 316 and a speed governor 320 can provide the highly controlled movement needed to actuate the illuminator 308 via the holder 314 to move the focus of the interrogating radiation 324 while data is collected by the data collection system 302. Here, the visible target 306 facilitates alignment of the subject's eye and, more particularly, the target tissue during scanning.

In other embodiments, the device can be substantially as described above but binocular. Here, the illuminator 108 can illuminate the target tissue of a pair of eyes with interrogating radiation simultaneously. In some embodiments, the illuminator 108 can comprise a pair of illuminators, each illuminator corresponding to each eye. Additionally or alternatively, the detector system 110 can comprise a plurality of detectors, each of the plurality of detectors associated with one of the pair of illuminators. Here, each of the patient's eyes is analyzed separately.

Figure 4:
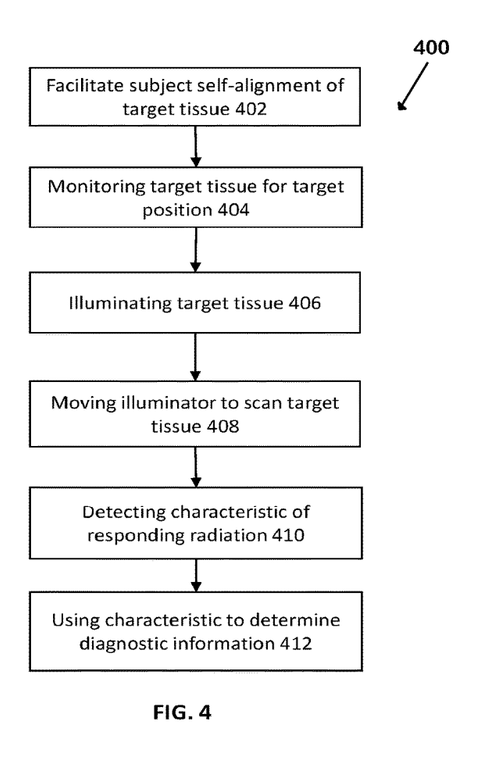
FIG. 4 illustrates one exemplary method according to the present subject matter.

As illustrated in FIG. 4, the present subject matter also provides for a method 400 that can comprise the steps of: facilitating subject self-alignment of a target tissue relative to a device 402, the device comprising: a data collection system comprising an illuminator, a detector and a beam splitter operably coupled to the detector; an actuation assembly coupled to the illuminator via a holder, the actuation assembly comprising a motor coupled to a linear actuator and a speed governor; and a visible target to facilitate alignment of the subject's eye with the data collection system; monitoring the target tissue to until the target tissue corresponds to a target position 404; illuminating the target tissue with the illuminator 406; moving the illuminator from a first position to a second position via the actuation assembly to scan a focal point of the interrogating light through a predefined thickness of the target tissue 408; detecting at least one characteristic of responding radiation received from or reflected from the target tissue 410; and correlating the at least one characteristic of responding radiation to determine specific diagnostic information comprising at least one of the presence, non-presence, onset, and duration of a pathological condition 412. The at least one characteristic of responding radiation comprises fluorescence data or scattering data. The method can further comprise transmitting the at least one characteristic of responding radiation to a remotely-located computational system via a transmitter operably coupled to the data collection system subsequent to detecting the at least one characteristic of responding radiation. The method can further comprise processing the at least one characteristic of responding radiation to determine specific diagnostic information. The method can even further comprise wirelessly transmitting the specific diagnostic information from the remotely-located computational system to the device, the device further comprising a receiver for receiving the specific diagnostic information. Here, the device only detects the at least one characteristic of responding radiation when the detector indicates the target tissue is in a target position.

Figure 5:
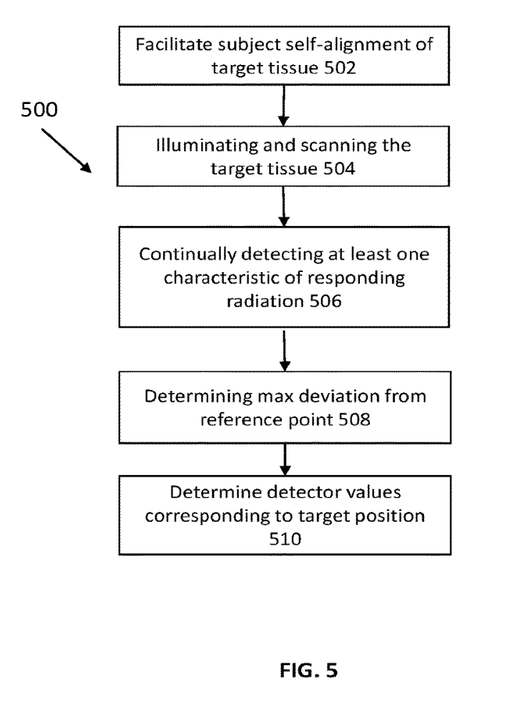
FIG. 5 illustrates another exemplary method according to the present subject matter.

In another embodiment illustrated in FIG. 5, the present subject matter provides for a method 500 substantially as described above, including facilitating subject self-alignment of the target tissue 502 and illuminating and scanning the target tissue 504, but the device can continually detect the at least one characteristic of responding radiation 506 and the data collection system 510 or the data processing system can determine which measured values of the at least one characteristic of responding radiation correspond to detector values that indicate the target tissue is in the target position. This can include determining an absolute value of an error of the detector measurement as a deviation from zero or a reference point as a basis for filtering the collected data 508.

In some embodiments, correlating the at least one characteristic of responding radiation to determine specific diagnostic information further comprises comparing the at least one characteristic with like values based on a normed population. The normed population can be age-normed, gender-normed, or ethnicity-normed. In some embodiments, correlating the at least one characteristic of responding radiation to determine specific diagnostic information can further comprise determining the amount the at least one characteristic varies from the like values of the normed population.

VARIOUS NOTES AND EXAMPLES

Example 1 is a device, comprising: a data collection system comprising an illuminator, a detector and a beam splitter operably coupled to the detector; an actuation assembly coupled to the illuminator via a holder, the actuation assembly comprising a motor coupled to a linear actuator; and a visible target to facilitate alignment of the subject's eye with the data collection system; wherein the illuminator illuminates the target tissue with interrogating radiation and the actuation assembly moves the illuminator from a first position to a second position to scan a focal point of the interrogating radiation through a predefined thickness of the target tissue; and wherein the detector detects at least one value of at least one characteristic of responding radiation received from or reflected from the target tissue.

In Example 2, the subject matter of Example 1 optionally includes wherein the responding radiation comprises back-scattered light, Rayleigh light, fluorescent light, or light generated by the target tissue in response to illumination.

In Example 3, the subject matter of any one or more of Examples 1-2 optionally include wherein the at least one value of the at least one characteristic of responding radiation received from or reflected from the tissue comprises intensity of the responding radiation or temporal characteristics of the responding radiation.

In Example 4, the subject matter of Example 3 optionally includes wherein temporal characteristics of the responding radiation comprise decay time of fluorescent emissions, phase shift characteristics, or polarization anisotropy characteristics.

In Example 5, the subject matter of any one or more of Examples 1-4 optionally include wherein the detector comprises an avalanche photodiode.

In Example 6, the subject matter of any one or more of Examples 1-5 optionally include wherein the illuminator comprises a light-emitting diode or a laser diode.

In Example 7, the subject matter of Example 6 optionally includes wherein the illuminator further comprise a first lens positioned with respect to the light source to produce interrogating radiation.

In Example 8, the subject matter of any one or more of Examples 6-7 optionally include wherein the illuminator has an operating wavelength of from about 400 to about 600 nm.

In Example 9, the subject matter of Example 8 optionally includes wherein the illuminator has an operating wavelength of from about 400 to about 460 nm.

In Example 10, the subject matter of any one or more of Examples 8-9 optionally include wherein the illuminator has an operating wavelength of 434 nm and a tolerance of about 10 nm.

In Example 11, the subject matter of any one or more of Examples 8-9 optionally include wherein the illuminator has an operating wavelength of 472 nm and a tolerance of about 10 nm.

In Example 12, the subject matter of any one or more of Examples 8-10 optionally include wherein the illuminator further comprises a lens system that is optically responsive to the interrogating radiation, wherein the lens system comprises at least one second lens, and an aperture at a lens system focus having a diameter of at least about 15 micrometers.

In Example 13, the subject matter of any one or more of Examples 1-12 optionally include wherein the motor comprises an electromechanically actuated motor.

In Example 14, the subject matter of any one or more of Examples 1-13 optionally include wherein the motor comprises a spring-wound motor.

In Example 15, the subject matter of Example 14 optionally includes a manual spring tensioner coupled to the spring-wound motor that is adjustable by a user.

In Example 16, the subject matter of any one or more of Examples 1-15 optionally include wherein the device is binocular.

In Example 17, the subject matter of Example 16 optionally includes wherein the illuminator illuminates the target tissue of a pair of eyes with interrogating radiation simultaneously.

In Example 18, the subject matter of any one or more of Examples 1-16 optionally include a data processing system including a transmitter for wirelessly transmitting the at least one value of the at least one characteristic of responding radiation to a remotely-located computational system.

In Example 19, the subject matter of Example 18 optionally includes wherein the data processing system further includes a receiver for wirelessly receiving specific diagnostic information from the remotely-located computational system.

In Example 20, the subject matter of any one or more of Examples 1-19 optionally include wherein the illuminator comprises a plurality of illuminators.

In Example 21, the subject matter of Example 20 optionally includes wherein the detector comprises a plurality of detectors, each of the plurality of detectors associated with a corresponding one of the plurality of illuminators.

In Example 22, the subject matter of any one or more of Examples 1-21 optionally include wherein the actuation assembly further comprises a speed governor operably coupled to the motor or the linear actuator.

Example 23 is a method, comprising: facilitating subject-self alignment of a target tissue relative to a device comprising: a data collection system comprising an illuminator, a detector and a beam splitter operably coupled to the detector; an actuation assembly coupled to the illuminator via a holder, the actuation assembly comprising a motor coupled to a linear actuator; and a visible target to facilitate alignment of the subject's eye with the data collection system; monitoring the target tissue to until the target tissue corresponds to a target position; illuminating the target tissue with the illuminator; moving the illuminator from a first position to a second position via the actuation assembly to scan a focal point of the interrogating light through a predefined thickness of the target tissue; detecting at least one characteristic of responding radiation received from or reflected from the target tissue; and correlating the at least one characteristic of responding radiation to determine specific diagnostic information comprising the presence, non-presence, onset, or duration of a pathological condition.

In Example 24, the subject matter of Example 23 optionally includes wherein the at least one characteristic of responding radiation comprises fluorescence data or scattering data.

In Example 25, the subject matter of any one or more of Examples 23-24 optionally include transmitting the at least one characteristic of responding radiation to a remotely-located computational system via a transmitter operably coupled to the data collection system subsequent to detecting the at least one characteristic of responding radiation.

In Example 26, the subject matter of Example 25 optionally includes processing the at least one characteristic of responding radiation to determine specific diagnostic information.

In Example 27, the subject matter of Example 26 optionally includes wirelessly transmitting the specific diagnostic information from the remotely-located computational system to the device, the device further comprising a receiver for receiving the specific diagnostic information.

In Example 28, the subject matter of any one or more of Examples 23-27 optionally include wherein correlating the at least one characteristic of responding radiation to determine specific diagnostic information further comprises comparing the at least one characteristic with like values based on a normed population.

In Example 29, the subject matter of Example 28 optionally includes wherein the normed population is age-normed, gender-normed, or ethnicity-normed.

In Example 30, the subject matter of Example 29 optionally includes determining the amount the at least one characteristic varies from the like values of the normed population.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A device, comprising:
   a data collection system comprising an illuminator, a detector and a beam splitter operably coupled to the detector;
   an actuation assembly coupled to the illuminator via a holder, the actuation assembly comprising a motor coupled to a linear actuator; and
   a visible target to facilitate alignment of the subject's eye with the data collection system;
   wherein the illuminator illuminates the target tissue with interrogating radiation and the actuation assembly moves the illuminator from a first position to a second position to scan a focal point of the interrogating radiation through a predefined thickness of the target tissue;
   wherein the detector detects at least one value of at least one characteristic of responding radiation received from or reflected from the target tissue; and
   wherein the motor comprises a spring-wound motor.

2. The device of claim 1, wherein the responding radiation comprises backscattered light, Rayleigh light, fluorescent light, or light generated by the target tissue in response to illumination.

3. The device of claim 1, wherein the at least one value of the at least one characteristic of responding radiation received from or reflected from the tissue comprises intensity of the responding radiation or temporal characteristics of the responding radiation.

4. The device of claim 3, wherein temporal characteristics of the responding radiation comprise decay time of fluorescent emissions, phase shift characteristics, or polarization anisotropy characteristics.

5. The device of claim 1, wherein the detector comprises an avalanche photodiode.

6. The device of claim 1, wherein the illuminator comprises a light-emitting diode or a laser diode.

7. The device of claim 6, wherein the illuminator further comprise a first lens positioned with respect to the light source to produce interrogating radiation.

8. The device of claim 6, wherein the illuminator has an operating wavelength of from about 400 to about 600 nm.

9. The device of claim 8, wherein the illuminator has an operating wavelength of from about 400 to about 460 nm.

10. The device of claim 8, wherein the illuminator has an operating wavelength of 434 nm and a tolerance of about 10 nm.

11. The device of claim 8, wherein the illuminator has an operating wavelength of 472 nm and a tolerance of about 10 nm.

12. The device of claim 8, wherein the illuminator further comprises a lens system that is optically responsive to the interrogating radiation, wherein the lens system comprises at least one second lens, a lens system focus, and an aperture at the lens system focus having a diameter of at least about 15 micrometers.

13. The device of claim 1, wherein the motor comprises an electromechanically actuated motor.

14. The device of claim 1, further comprising a manual spring tensioner coupled to the spring-wound motor that is adjustable by a user.

15. The device of claim 1, wherein the device is binocular.

16. The device of claim 15, wherein the illuminator illuminates the target tissue of a pair of eyes with interrogating radiation simultaneously.

17. The device of claim 1, further comprising a data processing system including a transmitter for wirelessly transmitting the at least one value of the at least one characteristic of responding radiation to a remotely-located computational system.

18. The device of claim 17, wherein the data processing system further includes a receiver for wirelessly receiving specific diagnostic information from the remotely-located computational system.

19. The device of claim 1, wherein the illuminator comprises a plurality of illuminators.

* * * * *